(12) United States Patent
Mueller, Jr. et al.

(10) Patent No.: US 7,311,673 B2
(45) Date of Patent: Dec. 25, 2007

(54) BIOPSY DEVICE

(75) Inventors: Richard L. Mueller, Jr., Jackson, WY (US); Paul K. Hsei, San Jose, CA (US)

(73) Assignee: Acueity, Inc., Hayward, CA (US)

( * ) Notice: Subject to any disclaimer, the term of this patent is extended or adjusted under 35 U.S.C. 154(b) by 378 days.

(21) Appl. No.: 10/422,381

(22) Filed: Apr. 24, 2003

(65) Prior Publication Data

US 2004/0215103 A1 Oct. 28, 2004

(51) Int. Cl.
*A61B 10/00* (2006.01)
(52) U.S. Cl. .................................. 600/564; 600/567
(58) Field of Classification Search ................ 600/562, 600/564–568; 606/159
See application file for complete search history.

(56) References Cited

U.S. PATENT DOCUMENTS

| | | | |
|---|---|---|---|
| 4,781,186 A | 11/1988 | Simpson et al. ............. 128/305 |
| 4,926,858 A | 5/1990 | Gifford, III et al. ......... 606/159 |
| 4,979,951 A | 12/1990 | Simpson ..................... 606/159 |
| RE33,569 E | 4/1991 | Gifford, III et al. ......... 606/159 |
| 5,047,040 A | 9/1991 | Simpson et al. ............. 606/159 |
| 5,053,044 A | 10/1991 | Mueller et al. .............. 606/159 |
| 5,441,510 A | 8/1995 | Simpson et al. ............. 606/159 |
| 5,571,130 A | 11/1996 | Simpson et al. ............. 606/171 |
| 5,706,812 A * | 1/1998 | Strenk et al. ................ 600/417 |
| 5,916,229 A * | 6/1999 | Evans ......................... 606/171 |
| 6,022,362 A * | 2/2000 | Lee et al. .................... 606/159 |
| 6,086,544 A | 7/2000 | Hibner et al. ............... 600/568 |
| 6,120,462 A | 9/2000 | Hibner et al. ............... 600/566 |
| 6,302,852 B1 * | 10/2001 | Fleming et al. ............. 600/567 |
| 6,432,064 B1 | 8/2002 | Hibner et al. ............... 600/564 |
| 6,432,065 B1 | 8/2002 | Burdorff et al. ............ 600/566 |
| 6,514,215 B1 * | 2/2003 | Ouchi ......................... 600/564 |
| 6,749,576 B2 * | 6/2004 | Bauer .......................... 600/567 |
| 6,758,824 B1 * | 7/2004 | Miller et al. ................. 600/568 |
| 2004/0077971 A1 * | 4/2004 | Vetter et al. ................. 600/564 |

* cited by examiner

*Primary Examiner*—Max Hindenburg
*Assistant Examiner*—Jonathan Foreman
(74) *Attorney, Agent, or Firm*—Olson & Cepuritis, Ltd.

(57) ABSTRACT

A biopsy device comprises a biopsy instrument, suitable for collecting at least one tissue sample from a body lumen, such as a mammary duct, and a cutter introducer sized for receiving the biopsy instrument and introducing the biopsy instrument into a mammary duct to retrieve a tissue sample therefrom.

38 Claims, 6 Drawing Sheets

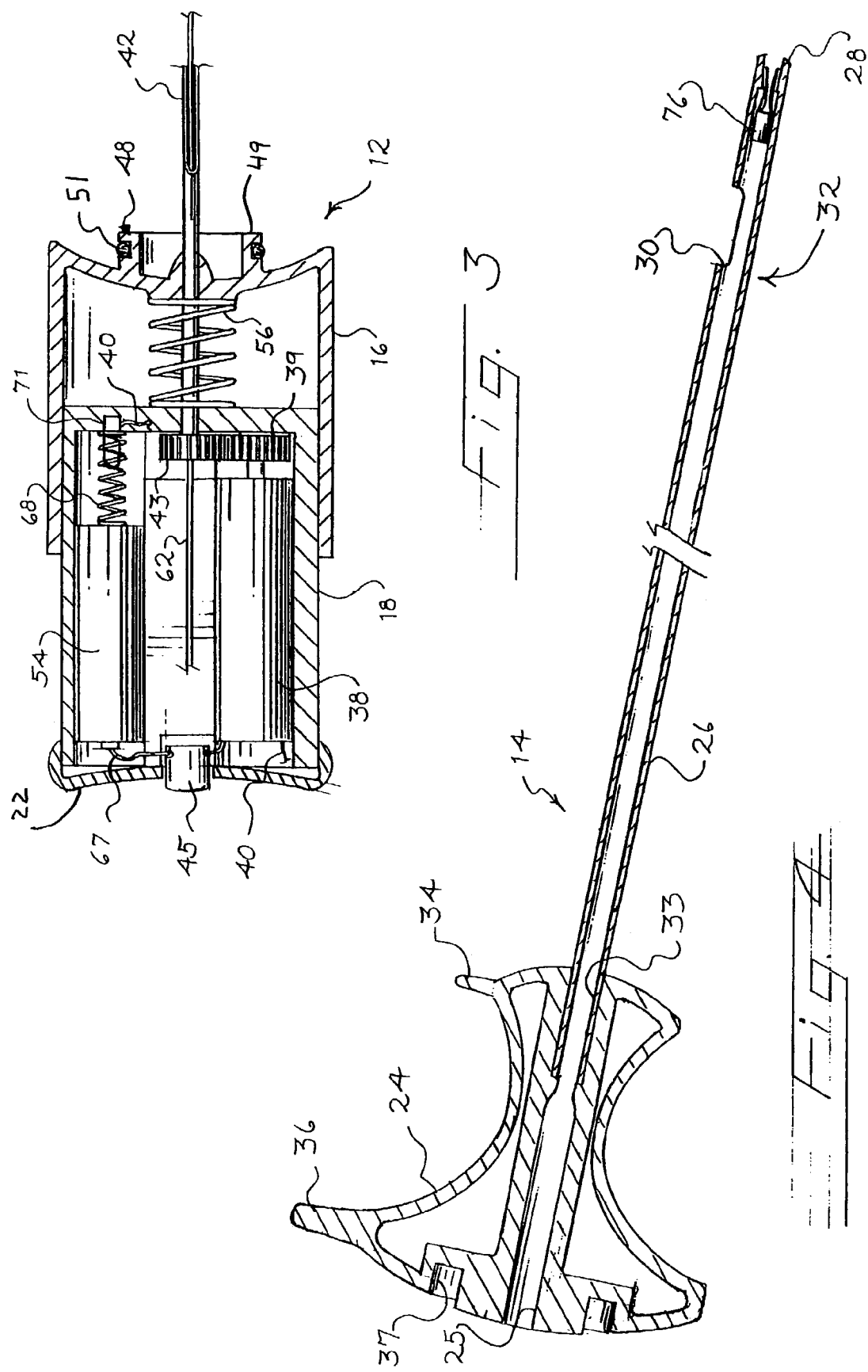

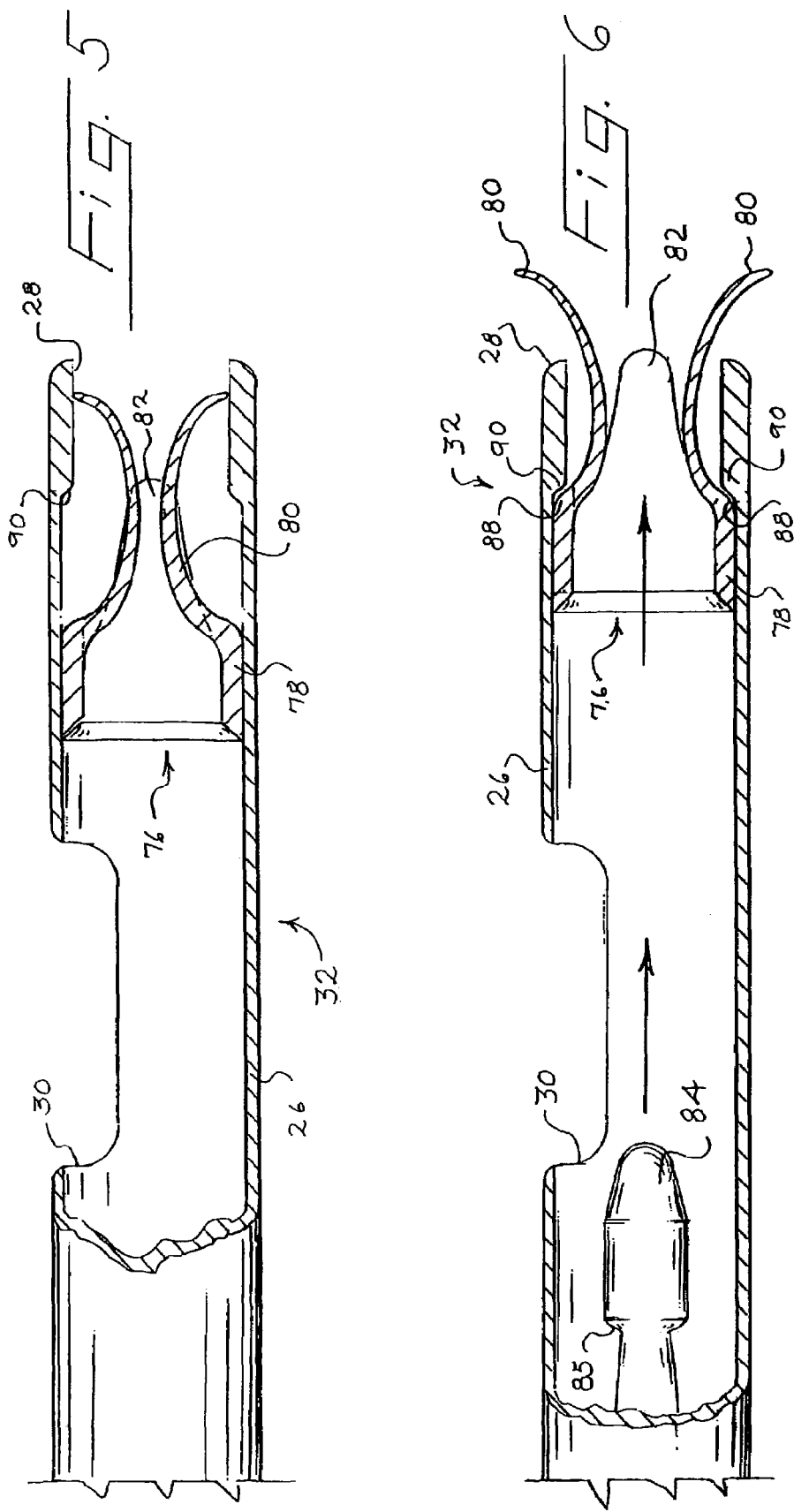

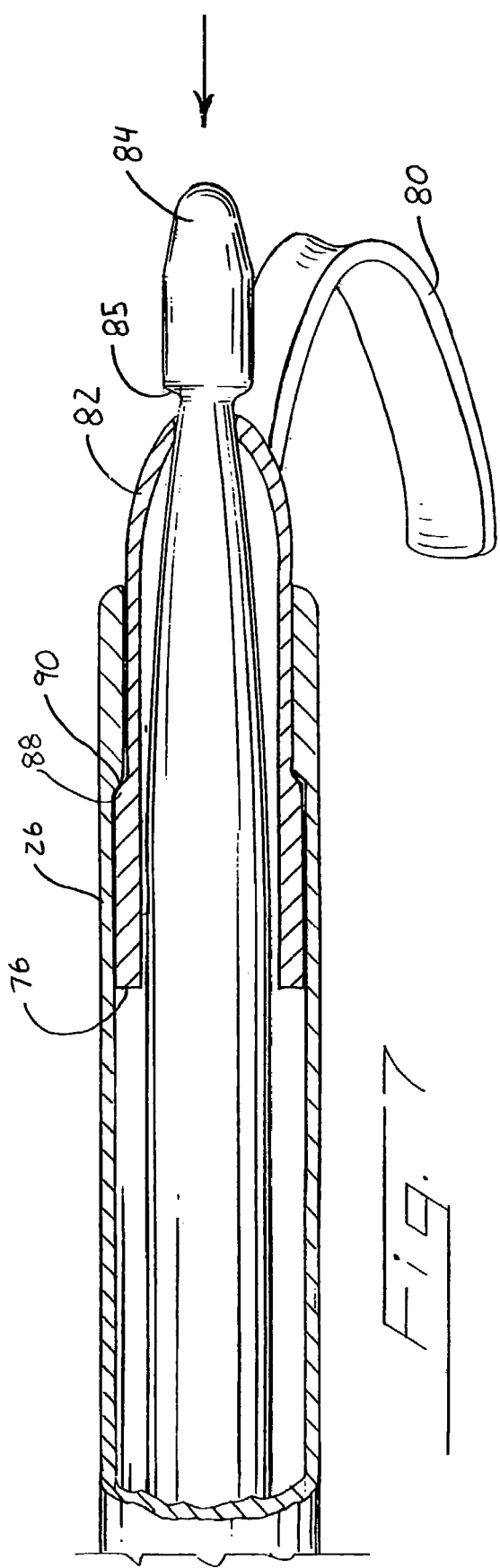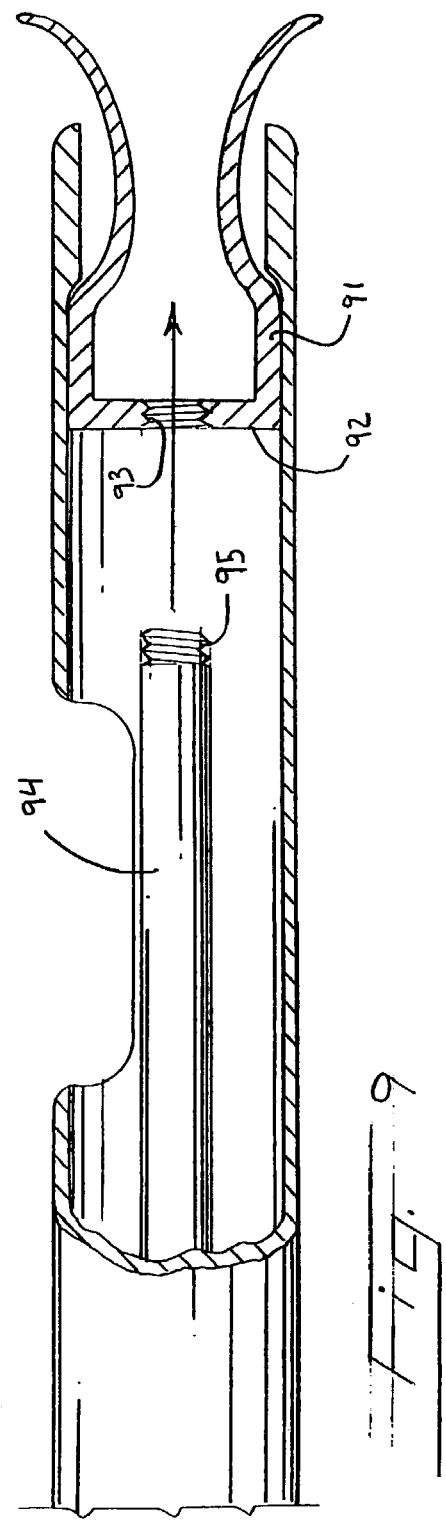

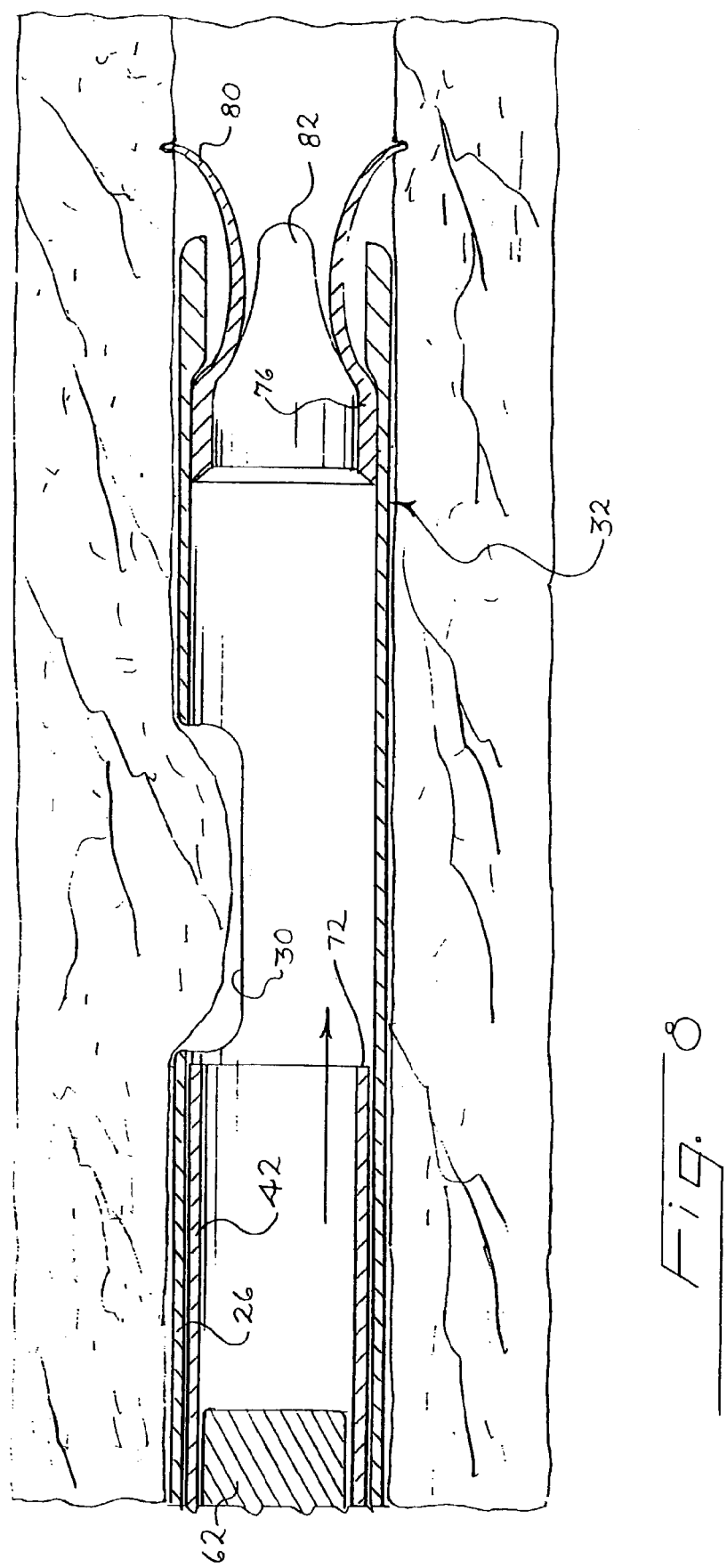

BIOPSY DEVICE

TECHNICAL FIELD OF THE INVENTION

The invention generally relates to a device for obtaining mammary duct tissue samples for analysis. More specifically, the invention relates to a biopsy device and an introducer therefor.

BACKGROUND OF THE INVENTION

Breast cancer is one of the health threats most feared by women, and is indeed the most common form of cancer in women. A key to treatment is early detection. For example, an annual mammogram is a method that has been used in hopes of early detection of breast cancer. One problem with mammography is that such an imaging technique can only find breast cancer once it has taken form. All too often, breast cancer is discovered at a stage that is too far advanced, when therapeutic options and survival rates are severely limited. While breast cancer is most common among women, in rare instances the human male may also have occurrences of breast cancer.

Other methods of detecting breast cancer are based on the fact that in a vast majority of instances breast cancer begins in the lining of mammary ducts. Studies have shown that fluid within the mammary duct contains high levels of breast cancer markers, and that an estimated 80%-90% of all breast cancers occur within the intraductal epithelium of the mammary glands. Fluid within the breast ducts contains an assemblage and concentration of hormones, growth factors and other potential markers comparable to those secreted by, or acting upon, the surrounding cells of the alveolar-ductal system. Likewise, mammary fluid typically contains cells and cellular debris or products that can also be used in cytological or immunological assays. As such, techniques such as ductal lavage, collection of mammary duct discharge, and brushing biopsies have been utilized to obtain such samples for diagnostic purposes.

In either event, once suspicious tissue is located, a biopsy of the tissue may then be taken. One biopsy device that has been utilized is the Mammotome® biopsy system available from Ethicon Endo-surgery, Inc., Cincinnati, Ohio. After mapping an area to be biopsied, the Mammotome® probe, a needle-like device with a hollow passage therethrough, is introduced through an incision cut into the breast and inserted with a sharpened distal end until the desired biopsy region is accessed. When the probe is positioned at the region of concern, tissue is received into a window in the probe with vacuum assist. A cutter then cuts and removes tissue samples for examination. The samples are passed through the hollow passage of the probe into a collection chamber. Because the Mammotome® probe is directional, multiple specimens can be collected without having to remove and reinsert the device. The Mammotome® probe is removed after the samples have been collected, and the incision is closed.

Such a system significantly decreases the invasiveness of the biopsy procedure by only requiring a small incision and puncture, which may be done under local anesthetic. However, in certain situations, such as where the tissue to be biopsied is in a mammary duct, the incision and probe insertion required with the Mammotome® is unnecessarily invasive and undesirable.

What is needed is a biopsy device for conducting a minimally invasive biopsy procedure without the need for an incision or anesthetic. It is also desirable that the physician be able to take multiple tissue samples from a single biopsy site. It is further desirable for the physician to be able to identify and record the location of each sample of tissue extracted. The present invention meets the foregoing desires and provides an improved device for taking a biopsy within a mammary duct, as well as a device that facilitates memorializing in the patient's records the location of the tissue sampled.

SUMMARY OF THE INVENTION

A biopsy device comprises a biopsy instrument provided with a tissue cutter and suitable for collecting at least one tissue sample from a body lumen, such as a mammary duct, and a cutter introducer sized for receiving the tissue cutter and guiding the biopsy cutter into a mammary duct.

The biopsy instrument includes a holster, a housing reciprocably mounted in the holster, and an elongated hollow cutter that extends from the housing and is driven by a cutter drive motor situated within the housing. A power connector, operably connected to a power source, is associated with the cutter drive motor. The hollow cutter rotates about a longitudinal axis thereof upon energization of the motor by activating a switch operably associated with the motor. The hollow cutter also extends distally relative to the holster when the housing is urged into the holster. A pusher rod assembly is removably mounted to the housing and received within the cutter. The pusher rod assembly preferably comprises a piston which is slidably received within the hollow cutter and may be extended therethrough. A coupling mount for removably receiving the cutter introducer, such as a boss terminating in a distal, radially outwardly extending flange, is also provided on the biopsy cutter.

Preferably included within the housing is a power source, such as a battery, which can be a primary battery, i.e., single use, or a secondary battery, i.e., rechargeable. Alternatively, the power source may be external to the housing and the holster therefor, but operatively connected to the power connector. The housing and holster are preferably formed of a lightweight rigid plastic. The cutter is preferably formed of a lightweight metal such as stainless or surgical steel, and the like.

The other component of the biopsy device is the cutter introducer, which is comprised of a hollow handle, and an elongated sheath having open opposite ends, i.e., a distal end and a proximal end, mounted to the handle and adapted to receive the cutter element therewithin. A cut-out or aperture is provided at a distal end portion of the sheath. A proximal end portion of the sheath is fixed within the handle. The hollow handle further defines an axial passage leading to the sheath.

The handle of the cutter introducer preferably includes an integrally formed azimuth indicator, which may be unitary with the handle. The azimuth indicator can also be a pair of azimuth indicators aligned vis-a-vis one another. The handle can also include a socket for receiving the coupling mount of the biopsy instrument. For example, the coupling socket on the handle may be an annular cavity which can receive the boss of the holster provided with a radially outwardly extending flange. The handle is also preferably formed of a lightweight rigid plastic.

A tissue anchor extendable through the introducer is desirable in some cases. The tissue anchor can comprise a hollow hub and flexible outwardly biased tines that extend from the hub and an optional retriever rod. The tissue anchor is slidably and rotatably mounted within the sheath at the distal end portion thereof. The tines of the anchor are extendable from the open distal end of the sheath and spread radially outwardly when so extended. A distal end portion of the retriever rod, which retracts the anchor and the tines within the sheath, is configured to engage the anchor.

In order to obtain a tissue sample with the biopsy device from a mammary duct the cutter introducer is first inserted into a nipple orifice at the nipple surface and then advanced into the mammary duct. An endoscope may be utilized within the introducer to locate and view the biopsy site, if desired. When a tissue mass of interest is located, and the distal end portion of the sheath positioned as desired, the tines of the anchor are extended beyond the open distal end by urging the hub of the tissue anchor to slide towards the distal end. The tines are pushed through the open distal end, and because they are outwardly biased, spread out radially to contact the walls of the mammary duct and immobilize the introducer.

The biopsy instrument, in particular the cutter, is inserted into the introducer and extended towards the distal end portion thereof. A tissue mass from the biopsy site is received within the introducer sheath through an aperture or cut-out at the distal end portion of the introducer sheath. The motor for driving the cutter element is energized and rotates the cutter element. As the distal end of the cutter travels across the aperture, that portion of the tissue mass received within the introducer sheath is severed. The biopsy instrument is withdrawn from the introducer sheath after the desired tissue samples have been taken. The hollow cutter element receives the tissue mass within its interior, and the severed tissue is later ejected from the hollow cutter by a pusher rod assembly for analysis.

When it is desired to remove the introducer, a retriever rod may be extended through the introducer sheath to engage the hub of the tissue anchor. The retriever rod is then retracted and draws the anchor back into the sheath, thereby disengaging the tines from the mammary duct. The introducer can then be withdrawn from the mammary duct. Alternatively, the anchor can be urged past the distal end of the introducer and left in the mammary duct as a biopsy site marker or indicator.

BRIEF DESCRIPTION OF THE DRAWINGS

In the drawings,

FIG. 3 is a partial cross sectional top view of the biopsy instrument of FIG. 2;

FIG. 4 is a cross sectional side view, partially broken, of the cutter introducer;

FIG. 5 is an enlarged cross sectional view of the distal end portion of the cutter introducer and the tissue anchor in a retracted position;

FIG. 6 is an enlarged cross sectional side view of the distal end portion of the cutter introducer with the tissue anchor in an extended position;

FIG. 7 is an enlarged cross sectional side view of the distal end portion of the biopsy introducer with the tissue anchor in an extended position and a retriever rod engaged with a tissue anchor latch;

FIG. 8 is an enlarged cross sectional side view of the distal end portion of the cutter introducer with the tissue anchor extended and engaged with a mammary duct, and a cutter within the introducer;

FIG. 9 is an enlarged cross sectional side view of the distal end portion of the biopsy introducer with an alternate embodiment of the tissue anchor in an extended position and equipped with a retriever rod suitable for engaging the tissue anchor.

DESCRIPTION OF THE PREFERRED EMBODIMENT OF THE INVENTION

Figure 1:
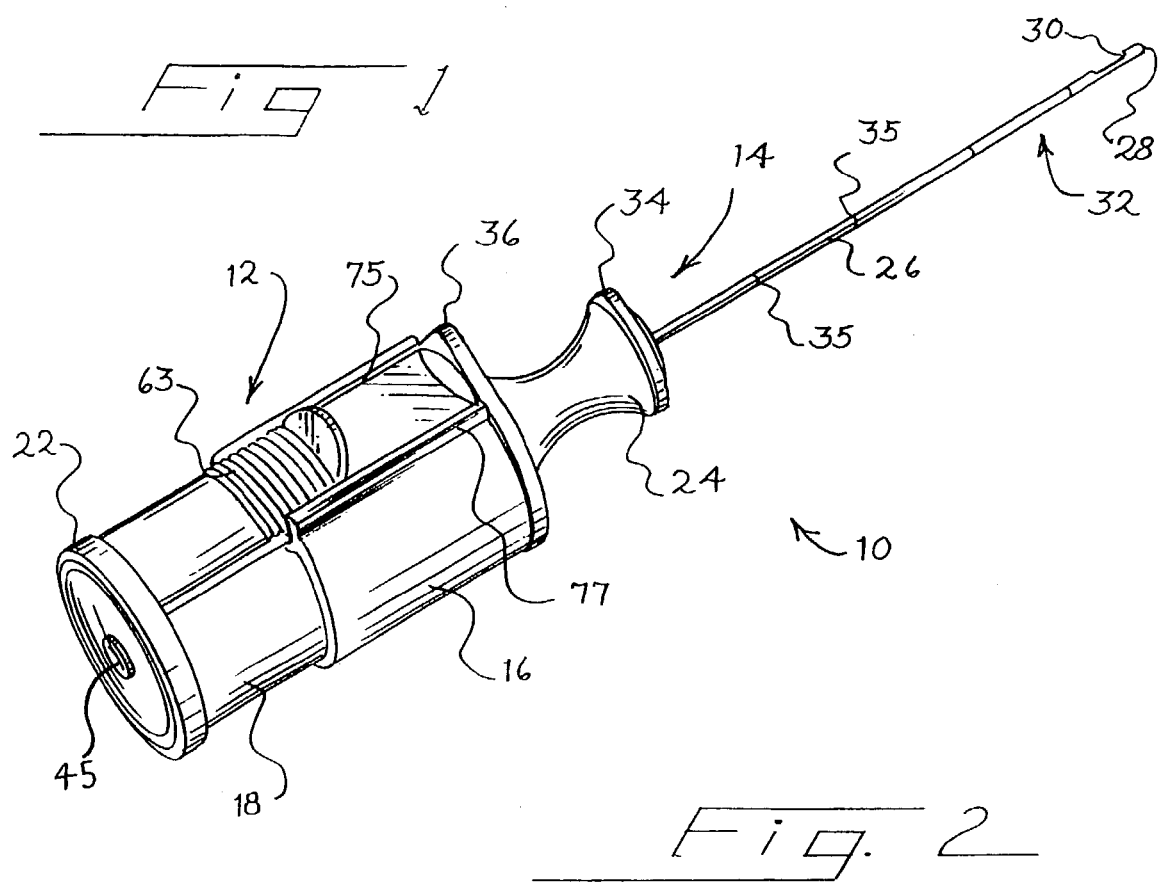
FIG. 1 is a perspective view of an embodiment of a biopsy device.

The invention disclosed herein is susceptible of embodiment in many different forms. Shown in the drawings and described hereinbelow in detail are preferred embodiments of the invention. It is to be understood, however, that the present disclosure is an exemplification of the principles of the invention and does not limit the invention to the illustrated embodiments.

A preferred embodiment of a biopsy device is shown in FIG. 1. Biopsy device 10 is comprised of a biopsy instrument 12 and a cutter introducer 14 removably carried by the biopsy instrument 12 and having hollow elongated sheath 26 mounted to handle 24. The biopsy instrument 12 comprises a holster 16, a housing 18 that is slidably and reciprocably received in holster 16, and a hollow elongated cutter 42 (FIG. 2), slidably received within elongated sheath 26 of cutter introducer 14. The elongated cutter 42 is driven by cutter motor 38 (FIG. 3) within housing 18. An end cap 22, removable to access various components within the housing 18, seals the proximal end of housing 18. An on-off switch, such as button switch 45 for energizing cutter motor 38 extends from the cap 22. Elongated sheath 26 has open opposite ends, i.e., a distal end 28 and a proximal end that is mounted to handle 24. A cut-out or aperture 30 is provided at a distal end portion 32 of the sheath 26. Depth indicators 35, axially spaced from one another can also be provided on sheath 26, if desired. Handle 24 is adapted for rotatable as well as removable mounting to housing 18, and includes a pair of integrally formed azimuth indicators, in particular, distal indicator 34 and proximal indicator 36, that are axially aligned with one another.

The cutter or blade 42 is configured for sliding travel through the handle 24 and sheath 26 of the introducer 14. Specifically, the outer diameter of the cutter 42 is smaller than the inner diameter of the sheath 26. The cutter 42 is also sufficiently long to extend to the distal end portion 32 of the sheath, and preferably such that when fully extended, the cutter element projects beyond the aperture 30.

Figure 2:
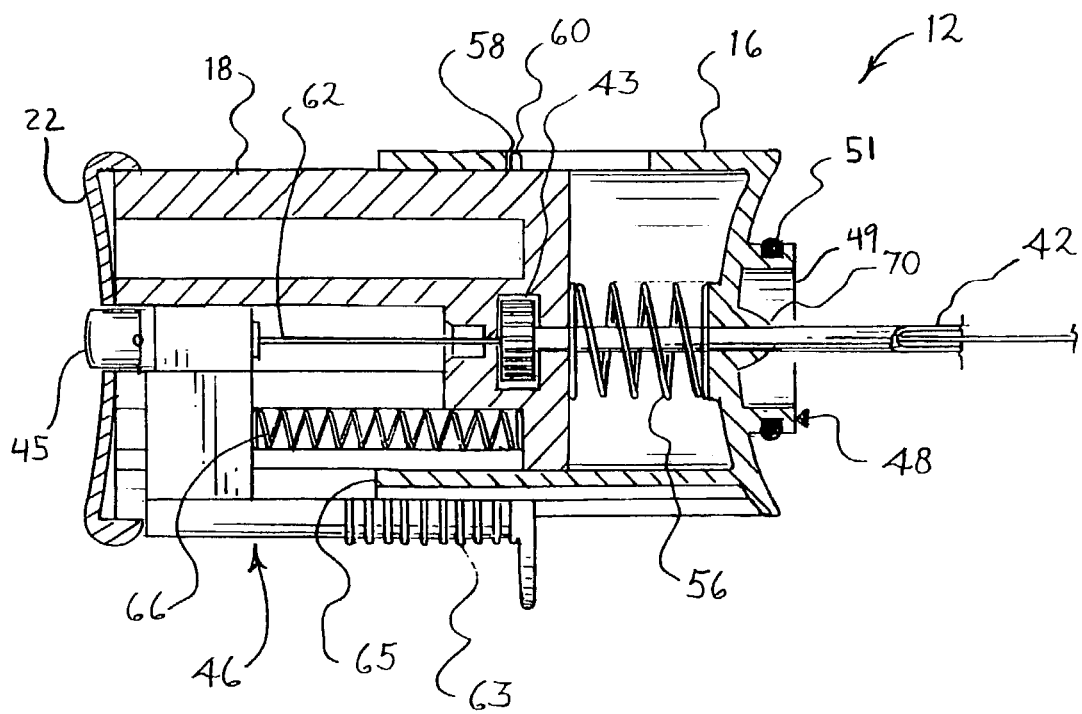
FIG. 2 is a partial cross sectional side view of the biopsy instrument.

As can be seen in FIGS. 2 and 3, a power connector, such as lead 40 for cutter drive motor 38 is also included in the housing 18 and is operably associated with the cutter drive motor 38 which drives hollow cutter 42 by rotating it about the longitudinal axis of the cutter introducer 14. In particular, motor 38 drives spur gear 39, which in turn is engaged with spur gear 43 secured to the proximal end portion of cutter 42. The motor 38 can be energized by any switching mechanism available in the art. For example, a two-position switch 45 can be operatively connected in a circuit between a power source and the motor 38, preferably biased in the OFF-position. Alternatively, the switch may also be formed by a battery 38 that serves as the power source and a conductive post 71 surrounded by insulated spring 68. As the housing is moved axially into the holster, battery 38 contacts post 71 to complete an electrical circuit between the motor and the battery. Thus, power lead 67, in cooperation with conductive post 71, spring 68 and power lead 40, form an electrical circuit between the cutter drive motor 38 and the battery 54. As yet another alternative, the switch and power supply can be operably connected to the motor, but situated external to the housing. For example, a foot-operated switch can be utilized in such instances.

Positioned between the distal end of holster 16 and distal end of housing 18 is a return spring, such as coil spring 56. The holster 16 further defines a groove 58 through which dorsal post 60 is positioned and extends therethrough from housing 18 (FIG. 2). The dorsal post 60 within the groove 58 serves as a stop to limit the longitudinal movement of the housing 18 relative to the holster 16, as well as to prevent rotational movement of the housing 18 relative to the holster 16.

Coil spring 56 is axially aligned with the cutter 42 in holster 16, through which cutter 42 is extended for axial reciprocation within elongated sheath 26. A hollow support or bearing 70 may also be provided within the holster 16, through which cutter 42 passes. Also provided by the holster 16 is a coupling mount 48 for removably attaching the biopsy instrument 12 to cutter introducer 14. The coupling mount 48 is preferably a boss 49 terminating in a distal, radially outwardly extending flange. Coupling mount 48 may also include an o-ring seal 51 that circumscribes boss 49.

A pusher rod assembly 46 includes elongated piston rod 62 and an actuator handle 63, and is removably mounted within the housing 18. The piston rod 62 is slidably received within the hollow cutter 42. The pusher rod assembly 46 is slidably positioned within housing 18, and actuator handle 63 is accessible from outside the housing for manual actuation. Further disposed within housing 18 is a pusher rod coil spring 66 biased against forward axial movement of the pusher rod assembly 46. Piston rod 62 extends from actuator handle 63 into and through cutter 42. Piston rod 62 has an outer diameter that is smaller than the inner diameter of the hollow cutter 42 such that any material within the cutter 42 is pushed out by piston rod 62 when extended. In particular, when pusher rod assembly 46 is pushed forward, piston rod 62 projects past the distal end 72 (FIG. 8) of the cutter 42, thereby clearing the hollow cutter 42 of any contents therein, such as tissue samples. Housing 18 further includes pusher stop 65 which limits the extent to which the pusher rod assembly 46 can be moved distally. The pusher rod assembly is guided by at least a holster track, defined by guide rail 75 and guide rail 77 (FIG. 1).

The other major component of the biopsy device is a cutter introducer removably mounted to holster 16. A cross section of a preferred embodiment of the biopsy introducer 14 is shown in FIG. 4. As discussed above, the cutter introducer 14 comprises a number of components, including hollow handle 24 and elongated sheath 26 having an aperture 30 formed at a distal end portion 32 of the sheath 26. The distal end 28 of sheath 26 preferably terminates in an atraumatic tip, such as a circumferential bevel. A proximal end portion 33 of the sheath 26 is fixed within the handle 24. An axial passage 25 is further defined by the hollow handle 24 and leads to sheath 26. Preferably the handle passage 25 is tapered so as to permit easier introduction of the cutter 42 or other instrument into the sheath 26. The handle 24 also defines an annular coupling socket 37 for rotatable mounting to coupling mount 48 of the biopsy instrument 12. In this embodiment, the socket 37 is configured to receive coupling mount 48 on holster 16 (FIGS. 2 and 3).

Also shown within the distal end portion 32 of sheath 26 thereof is tissue anchor 76. Tissue anchor 76 is optional and aids the operator in maintaining penetration control as indicated by depth marker 35. An externally applied nipple clamp (not shown) may be optionally employed to clamp or retain introducer sheath 26 within the nipple duct sphincter muscle, thereby also aiding in penetration control.

An enlarged view of the distal end portion 32 of the introducer is shown in FIGS. 5 and 6. Tissue anchor 76 comprises a hollow hub 78, flexible, outwardly biased tines 80 that extend from the hub 78, and a latch 82 which extends from the hub axially. The tissue anchor 76 is slidably and rotatably mounted within the distal end portion 32 of the sheath 26. Alternatively, tissue anchor 76 may be extended through the sheath 26 after an endoscopic viewing procedure has located the biopsy site. The anchor 76 can be partially or fully extendable through the open distal end 28 of the sheath 26, as desired. Latch 82 is configured to engage a distal end portion 86 of a retriever rod, which is discussed in further detail below.

Referring to FIG. 5, the tissue anchor 76 is shown in a retracted position. The tissue anchor 76 can be pushed partially through distal end 28 to extend the tines 80 until annular step 88 abuts beveled detent 90. The tissue anchor 76 may be pushed by any appropriate device, such as by an endoscope viewing assembly, push rod, or other instrument that is extendable through the sheath 26 to engage hub 78.

Referring to FIG. 6, the extent to which tissue anchor 76 can be extended through distal end 28 may be limited by hub 78 which includes an annular step 88, in cooperation with beveled detent 90 formed about the distal end portion 32. As the tines 80 are extended past the distal end 28, their outward bias causes the tines 80 to spread radially and engage the interior of the mammary duct (not shown). As such, the axial position of the sheath 26 within the mammary duct is secured. The hub 78, however, is sized to rotate relative to sheath 26. As such, the sheath 26 may be rotated about hub 78 within the mammary duct to reposition the circumferential orientation of aperture 30 even after the tissue anchor 76 has been engaged by manipulation of the handle 24 (FIG. 1). As will be discussed in further detail below, rotatable repositioning the aperture 30 permits collection of multiple tissue samples from the same region of a mammary duct.

Preferably, the annular step 88 and beveled detent 90 are contoured so that by application of additional force, the tissue anchor 76 can be urged past the distal end 28 of the sheath 26 and left in place as a marker for the biopsy site. Tactile feedback is provided to the operator by increased resistance from the interaction of annular step 88 and detent 90 when the anchor 76 is extended, but still within the sheath 26. Alternatively, tissue anchor 76 can be disengaged from sheath 26 by gently withdrawing sheath 26 from the biopsy site such that tissue anchor 76 is left behind still engaged with the mammary duct wall.

If it is desired to remove the anchor 76, preferably it is disengaged from the mammary duct by retraction into the sheath 26. In order to retract the anchor 76, a retriever rod 84 is introduced through the sheath 26. The retriever rod 84 includes a detent 85 for engaging the latch 82 extending from the hub 78 as shown in FIG. 7. The retriever rod 84 is then retracted from the introducer 14, thereby also retracting the anchor 76.

In order to obtain a tissue sample with the biopsy device 10 (FIG. 1), the cutter introducer 14 is first inserted into a mammary duct via a nipple orifice. The desired nipple orifice is first located through use of any means such as an illuminated nipple cup (not shown). A nipple orifice dilator or catheter (not shown) may be used to dilate the nipple orifice, if desired, to permit easier insertion of the introducer. An endoscope may be extended within the introducer to enable viewing of the biopsy site. When a desired mass of tissue is located, the anchor 76 is extended as described above, and as shown in FIG. 8. The hollow cutter 42 of the biopsy instrument is guided through the cutter introducer 14 and pushed towards the distal end portion 32 and the aperture 30. A tissue mass is received within the sheath 26 through the aperture or cut-out 30 at the distal end portion 32. The tissue mass can be urged into the aperture 30 by external pressure applied to the breast or alternatively with the aid of a vacuum, or by pressing the aperture against the desired biopsy area. The cutter motor 38 for driving the cutter 42 of the biopsy instrument can then be energized. Driven by motor 38, cutter 42 rotates and severs the portion of the tissue mass received within the sheath 26 as the distal end 72 of the cutter 42 travels across aperture 30. Preferably, the hollow cutter 42 receives the tissue mass within its interior. The biopsy instrument 12 is removed from the introducer 14 after the desired tissue sample is obtained, and the tissue sample is later expelled from the cutter 42 by piston rod 62 of the pusher rod assembly extending therethrough. Alternatively, the hollow cutter 42 may be operatively connected to a vacuum source for removal of the severed tissue sample through a central passageway defined by the hollow cutter 42.

An alternate embodiment of the tissue anchor and retriever rod are shown in FIG. 9. Anchor 91 has a configuration similar to the anchor discussed above, but includes a base 92 defining a threaded hole 93. Retriever rod 94 has a threaded distal end 95 that is threadably engageable with threaded hole 93. Anchor 91 can thereby extended to a desired degree and retracted by threadedly engaging retriever rod 94 with anchor 91 and extending or retracting the retriever rod 94.

Figure 10:
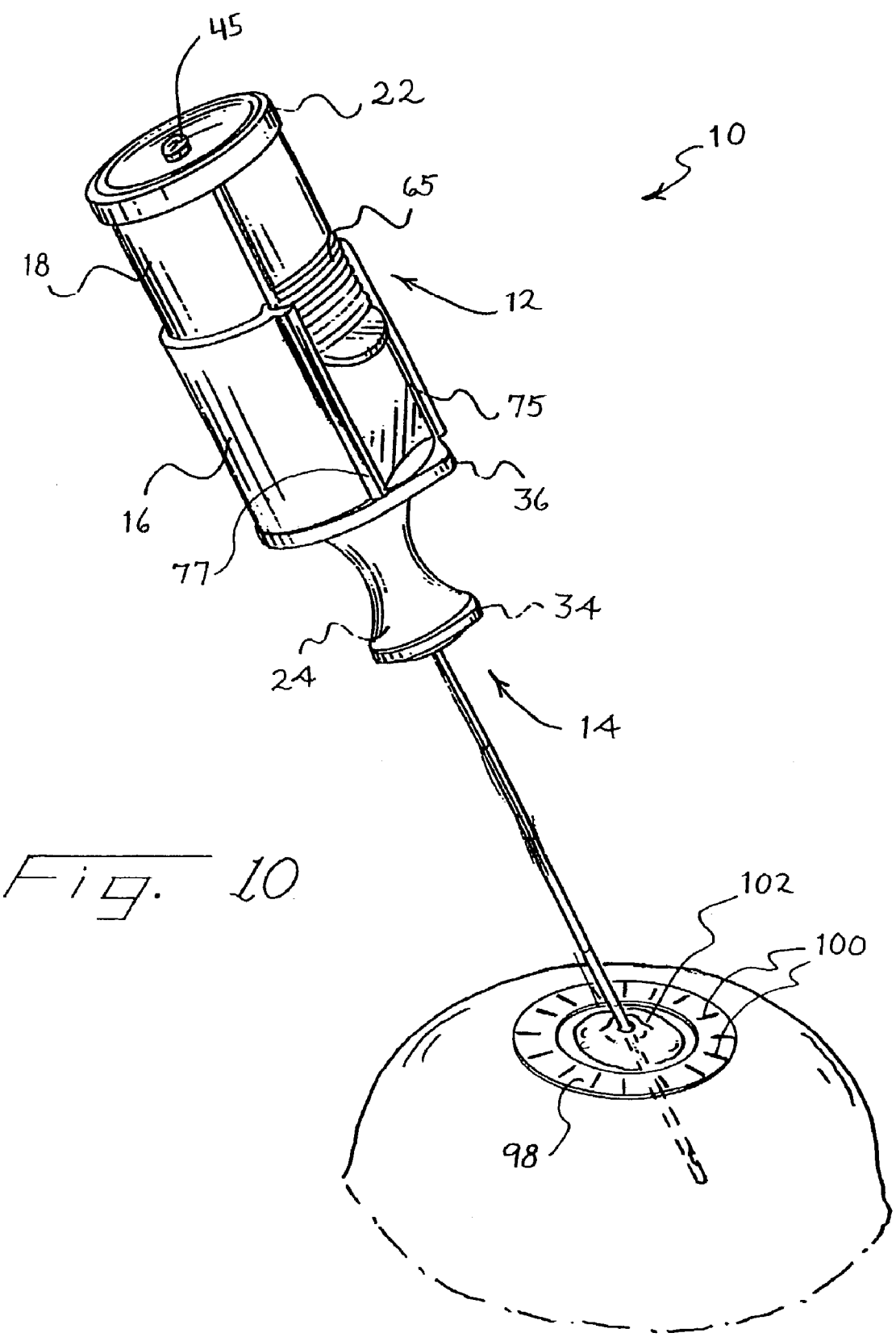
FIG. 10 is a schematic of a human breast having the biopsy device inserted therein, and an azimuth marker circumscribing a breast nipple.

To obtain multiple tissue samples from a biopsy site, and to discern the relative original locations of the tissue samples as part of the tissue analysis an azimuth marker is provided. To that end, and as illustrated in FIG. 10, an azimuth marker 98 having a plurality of circumferential marks 100, is provided and can be as part of a biopsy kit. Azimuth marker 98 is removably secured about a nipple 102, such as with a physiologically compatible pressure sensitive adhesive. The clinician notes how azimuthal indicators 34 and 36 align with circumferential marks 100 while the microendoscope is still positioned within introducer 14. The cooperation of the azimuthal indicators 34 and 36 and depth markers 35 establishes the location of the target tissue so that the microendoscope can be removed and the biopsy instrument 12 inserted. Utilizing the procedure discussed above, a tissue sample is obtained. As part of the procedure, the practitioner aligns the distal azimuthal indicator 34 and proximal azimuthal indicator 36 with a mark on the azimuth marker 98 and notes the indicator position. After a tissue sample is excised by the cutter 42, the biopsy instrument 12 is disengaged from the biopsy introducer 14. The practitioner extends the pusher rod assembly 46 by forwardly moving push rod handle 63, and thereby causing piston rod 62 (FIG. 8) to pass beyond the distal end of cutter 42 and eject the severed tissue sample. The tissue sample or samples may be collected on a collection tray having multiple recesses or numbered slots for tracking the source of the tissue sample. The biopsy instrument 12 can then be reinserted into the introducer 14, which is still held in place at the biopsy site by the tissue anchor 76, and rotated such that distal indicator 34 and proximal indicator 36 are aligned with a circumferential mark on azimuthal marker 98 different than that for prior tissue samples. In so doing, the aperture at the distal end portion of the introducer is repositioned to accept a tissue mass from a position adjacent to or near the previously excised tissue mass. The cutter then excises and retains a portion of this particular tissue. This sampling process is repeated as desired. For example, the practitioner can obtain tissue samples by aligning the distal indicator 34 and proximal indicator 36 with successive circumferential markers in a clockwise direction. Alternatively, multiple tissue samples can be obtained without retracting the biopsy instrument 12 from the introducer 14. In this case, the aperture 30 (FIG. 8) is positioned and the cutter 42 is rotated by the cutter drive motor 38 and passed across the aperture 30, which is then rotatably repositioned and the cutter is again rotated and passed across the newly positioned aperture 30. In so doing, multiple tissue samples are held within the hollow cutter 42. The cutter 42 is then removed and the multiple tissue samples ejected by the pusher rod assembly. As discussed, after the desired tissue samples are obtained, a retriever rod can be used to retract the anchor, and thereby, permit retraction of the introducer. If desired, the rod 64 of the pusher rod assembly may also serve as the retriever rod.

The foregoing descriptions are to be taken as illustrative, but not limiting. Still other variants within the spirit and scope of the present invention will readily present themselves to those skilled in the art.

The invention claimed is:

1. A biopsy device comprising:
    a biopsy instrument suitable for collection of at least one tissue sample from a biopsy site in a body lumen, the biopsy instrument comprising,
    a holster,
    a housing mounted in the holster for reciprocating movement,
    a cutter drive motor in the housing,
    a power source within the housing and operably associated with the cutter drive motor,
    a switch operably associated with the cutter drive motor and the power source for energizing the motor,
    a hollow cutter rotatably driven by the cutter drive motor and rotatably mounted in the housing,
    a pusher rod reciprocably mounted to the housing and slidably received within the hollow cutter element, and
    the holster including a coupling mount for removably receiving a cutter introducer; wherein the cutter introducer is sized for receiving the biopsy instrument and comprises;
    a hollow handle adapted for engagement with the coupling mount; a hollow elongated sheath having an open distal end and an open proximal end and defining a cut-out at a distal end portion;
    a proximal end portion of the sheath fixed in the handle; and
    the housing reciprocably movable with respect to the holster and the handle to reciprocate the cutter within the cutter introducer.

2. The biopsy device of claim 1, wherein the coupling mount is a boss terminating in a distal, radially outwardly extending flange.

3. The biopsy device of claim 1, wherein the introducer handle further includes a coupling socket for rotatable mounting to a biopsy device.

4. The biopsy device of claim 1, wherein the introducer is sized for removably receiving an endoscope viewing assembly.

5. The biopsy device of claim 1, wherein the switch is biased to the OFF-position.

6. The biopsy device of claim 1, further including tissue anchor slidably and rotatably mounted within the elongated sheath of the introducer at the distal end portion thereof and extendable therefrom.

7. The biopsy device of claim 6, wherein the tissue anchor comprises a hollow hub, at least one flexible outwardly biased tine extending from the hub, and a latch on the hub for engagement with a distal end portion of an elongated retriever rod.

8. The biopsy device of claim 1, wherein the introducer handle further includes at least one integral azimuth indicator.

9. The biopsy device of claim 8, wherein the azimuth indicator is unitary with the introducer handle.

10. The biopsy device of claim 8, wherein the introducer handle further includes a pair of spaced azimuth indicators.

11. The biopsy device of claim 1, further including an activator handle coupled to the pusher rod adapted to cause reciprocating movement by the pusher rod with respect to the housing.

12. The biopsy device of claim 11, wherein the power source is a battery.

13. The biopsy device of claim 12, wherein the battery is a primary battery.

14. The biopsy device of claim 12, wherein the battery is a secondary battery.

15. A biopsy kit comprising:
a biopsy device suitable for collection of a tissue sample from a biopsy site in a lumen, the biopsy device comprising:
a cutter introducer comprising a rigid elongated apertured hollow sheath rotatable about a longitudinal axis having a distal end portion and a proximal end portion, wherein the distal end portion includes an open distal end defining an atraumatic tip and an aperture spaced from the open distal end for receiving a tissue mass, and a hollow handle about the proximal end portion of the sheath including at least one azimuth indicator,
a biopsy instrument comprising an elongated cutter for severing the tissue mass received through the aperture, the cutter being sized for removable insertion in the biopsy introducer; and
an azimuth marker having encircling markings, whereby the azimuth indicator is suitable for alignment with the encircling markings.

16. The biopsy kit of claim 15, wherein the cutter is motor driven.

17. The biopsy kit of claim 15, wherein the cutter is suitable for collecting the tissue sample.

18. The biopsy kit of claim 15, wherein the sheath further includes axially spaced depth indicators thereon.

19. The biopsy kit of claim 15, wherein the distal end portion of the cutter introducer terminates in an atraumatic tip.

20. The biopsy kit of claim 19, wherein the distal end portion of the cutter introducer further includes a circumferential bevel spaced from the atraumatic tip.

21. The biopsy kit of claim 15, wherein the cutter introducer further comprises an anchor suitable for axially securing the distal end portion of the sheath at the biopsy site.

22. The biopsy kit of claim 21, wherein the anchor is extendable and retractable at the distal end portion of the sheath.

23. The biopsy kit of claim 22, wherein the anchor comprises at least one time.

24. The biopsy kit of claim 21, wherein the biopsy instrument includes a tissue ejector mechanism.

25. The biopsy kit of claim 24, wherein the tissue ejector mechanism is a pusher rod assembly.

26. The biopsy kit of claim 25, wherein the tissue ejector mechanism is a vacuum source operatively connected to the cutter.

27. A biopsy kit comprising:
a biopsy instrument suitable for collection of at least one tissue sample from a biopsy side in a lumen, the biopsy instrument comprising
a holster,
a housing reciprocably mounted in the holster,
a cutter drive motor in the housing,
a power source within the housing and operably associated with the cutter drive motor,
a switch operably associated with the cutter drive motor and the power source for energizing the motor,
a hollow cutter rotatably driven by the cutter drive motor and rotatably mounted in the housing,
a pusher rod reciprocably mounted to the housing and slidably received within the hollow cutter, and
the holster including a coupling mount for removably receiving a cutter introducer;
a cutter introducer sized for insertion into a mammary duct and for receiving the biopsy instrument therewithin, and comprising
a hollow handle including at least one azimuth indicator;
an elongated sheath having an open distal end terminating in a tip, an open proximal end defining a cut-out at a distal end portion thereof, spaced from the tip and having a proximal end portion of the sheath fixed in the handle; and
an azimuth marker for placement about a breast nipple and having circumferential markings, whereby the at least one azimuth indicator is suitable for alignment with the circumferential markings; and
the housing reciprocably movable with respect to the holster and the handle to reciprocate the cutter within the cutter introducer.

28. The biopsy kit of claim 27, wherein the coupling mount is a boss terminating in an distal radially outwardly extending flange.

29. The biopsy kit of claim 27, wherein the introducer handle further includes a pair of spaced azimuth indicators.

30. The biopsy kit of claim 27, wherein the introducer handle further includes a coupling socket for rotatable mounting to a coupling mount on the holster.

31. The biopsy kit of claim 27, wherein the introducer is sized for removably receiving an endoscope viewing assembly.

32. The biopsy kit of claim 27, wherein the switch is biased to the OFF-position.

33. The biopsy kit of claim 27, further including a tissue anchor slidably and rotatably mounted within the elongated sheath of the introducer at the distal end portion thereof and extendable therefrom.

34. The biopsy kit of claim 33, wherein the tissue anchor further comprises a hollow hub, at least one flexible outwardly biased tine extending from the hub, and a latch on the hub for engagement with a distal end portion of an elongated retriever rod.

35. The biopsy kit of claim 27, further including an activator handle coupled to the pusher rod adapted to cause reciprocating movement by the pusher rod with respect to the housing.

36. The biopsy kit of claim 35, wherein the power source is a battery.

37. The biopsy kit of claim 36, wherein the battery is a primary battery.

38. The biopsy kit of claim 37, wherein the battery is a secondary battery.

* * * * *